United States Patent
Hong

(10) Patent No.: US 10,500,757 B2
(45) Date of Patent: Dec. 10, 2019

(54) BAMBOO FENCE MAKING METHOD

(71) Applicant: ZHEJIANG HONGLI BAMBOO AND WOOD INDUSTRIAL CO., LTD., Anji County, Zhejiang Province (CN)

(72) Inventor: Ye Hong, Anji County (CN)

(73) Assignee: ZHEJIANG HONGLI BAMBOO AND WOOD INDUSTRIAL CO., LTD., Zhejiang Province (CN)

(*) Notice: Subject to any disclaimer, the term of this patent is extended or adjusted under 35 U.S.C. 154(b) by 317 days.

(21) Appl. No.: 15/491,251

(22) Filed: Apr. 19, 2017

(65) Prior Publication Data
US 2018/0305952 A1 Oct. 25, 2018

(51) Int. Cl.
B27K 9/00 (2006.01)
A01N 59/14 (2006.01)
C09D 191/00 (2006.01)
C09D 5/14 (2006.01)
C08L 93/04 (2006.01)
C08L 97/00 (2006.01)
B27J 1/00 (2006.01)
E04H 17/14 (2006.01)

(52) U.S. Cl.
CPC .............. B27K 9/002 (2013.01); A01N 59/14 (2013.01); C08L 93/04 (2013.01); C08L 97/002 (2013.01); C09D 5/14 (2013.01); C09D 191/00 (2013.01); B27J 1/00 (2013.01); B27J 1/006 (2013.01); E04H 17/14 (2013.01)

(58) Field of Classification Search
CPC .... B27K 9/002; B27K 2240/20; B27K 3/163; A01N 59/14; B27M 3/0046; B27M 1/04; D01B 1/36; B27N 1/00–029; B27N 3/00–28; B27N 5/00–02; B27N 7/00–005; B27N 9/00; B27C 71/009; B27C 2017/0018; B27C 71/02; B27C 2017/025; C01B 32/05; C01B 32/00; B27L 3/153; C08L 75/02; C08L 61/00; C08L 61/06; C08L 61/12; C08L 61/14; C08L 31/04; B27J 1/00; B27J 1/003; B27J 1/006; B27J 7/00
USPC ....... 144/333; 264/29.1, 155, 232, 322, 129, 264/345, 348, 29.2, 29.4, 29.5, 29.6, 29.7; 34/202; 202/100
See application file for complete search history.

(56) References Cited

U.S. PATENT DOCUMENTS

| | | | | |
|---|---|---|---|---|
| 5,916,105 A * | 6/1999 | Gow | ........................ | E04H 17/16 256/19 |
| 5,967,207 A * | 10/1999 | Chen | .......................... | B27J 1/00 144/3.1 |
| 5,972,467 A * | 10/1999 | Washo | ........................ | B27J 1/00 144/333 |
| 2002/0195169 A1* | 12/2002 | Chen | .......................... | B27J 1/00 144/347 |
| 2009/0324876 A1* | 12/2009 | Yang | .......................... | B32B 3/06 428/99 |
| 2017/0239836 A1* | 8/2017 | Zhan | ......................... | B27K 3/52 |

FOREIGN PATENT DOCUMENTS

| | | | | |
|---|---|---|---|---|
| CN | 104085028 A | 10/2014 | | |
| CN | 105365019 A | 12/2015 | | |
| CN | 105599082 A | 12/2015 | | |
| CN | 105599082 A * | 5/2016 | ............... | B27K 3/52 |
| CN | 105948040 A * | 9/2016 | | |
| JP | 2003082360 A * | 9/2001 | ............. | Y02E 50/14 |
| WO | WO-2015154635 A1 * | 10/2015 | ........... | B27K 3/0214 |

OTHER PUBLICATIONS

Guadua Bamboo, "Bending Bamboo by Applying Heat", Dec. 25, 2013, YouTube Video https://www.youtube.com/watch?v=r4IO3DVGRTw.*
Lin et al., "Application of Bamboo Vinegar with Process to Evaluate Fungi Resistance of Bamboo Materials", 2006, Faculty of Agriculture, Kyushu University.*
JP2003082360A Machine Translation.*
CN105599082A Machine Translation.*
CN105948040A Machine Translation.*

* cited by examiner

Primary Examiner — Adam J Eiseman
Assistant Examiner — Sarkis A Aktavoukian
(74) Attorney, Agent, or Firm — NK Patent Law

(57) ABSTRACT

The invention relates to a bamboo fence making method. The method comprises the following steps that (a) a bamboo material is made by adopting raw bamboos; (b) mold and insect prevention liquid is sprayed; (c) a bamboo fence is made; (d) heat treatment is performed; (e) water spraying is performed for cooling; (f) drying is performed. The made bamboo fence does not produce the adverse influence on the environment, also has an insect prevention effect, and the effect duration is at least 2 years.

10 Claims, No Drawings

BAMBOO FENCE MAKING METHOD

BACKGROUND OF THE INVENTION

Technical Field

The present disclosure relates to a bamboo processing method, in particular to a bamboo fence making method.

Description of Related Art

Serving as building materials, bamboo materials have broad applications, have the advantages of being lightweight, high strength and good toughness, but have the shortcoming of poor antiseptic property. Especially, when the bamboo materials serve as outdoor building materials such as bamboo fences, the adverse influences of air, water and ultraviolet rays on the materials also need to be considered. However, people have not developed anti-corrosion and weather-resistant bamboo materials at present.

BRIEF SUMMARY OF THE INVENTION

Accordingly, for solving the above technical problems, the present disclosure provides a bamboo fence making method.

The technical scheme for solving the above problems of the present disclosure is as follows:

A bamboo fence making method comprises the following steps:

(a) raw bamboos are straightened and cut to obtain a bamboo material having specified length or the raw bamboos are cut to reach the specified length and then are straightened to obtain a bamboo material;

(b) the bamboo material is put inside a hot baking room, baking is performed at the temperature of 180-250° C. for 2-3 hours, then mold and insect prevention liquid is sprayed, then cooling is performed to reach 150-180° C., the temperature is kept for 6-10 hours for heat treatment; then, the mold and insect prevention liquid is sprayed again, cooling continues to reach 50-150° C. and this temperature is kept for 3-6 hours to obtain a dried medicinal bamboo material;

(c) the dried medicinal bamboo material is punched and is serially connected by using iron wires to make a bamboo fence;

(d) the bamboo fence is put in a high-pressure carbonization furnace with the temperature of 120-200° C. and the air pressure of 0.2 MPa or above, heat treatment is performed for 3-5 hours to obtain a carbonized bamboo fence;

(e) the carbonized bamboo fence is cooled through water spraying to obtain a rehydrated carbonized bamboo fence;

(f) the rehydrated carbonized bamboo fence is dried at a low temperature of 45-60° C. to reach the moisture content of 10-18%, and a dried carbonized bamboo fence is obtained;

The mold and insect prevention liquid contains, by mass, the following components:

an antibacterial agent 1-6 parts
a loss-resistant agent 3-10 parts
a surface active agent 0.1-4 parts
a solvent 3.5-10 parts
water 2-6 parts The antibacterial agent is boric acid or borate, the loss-resistant agent is one or more of phenolic resin, urea resin, polyvinyl acetate, alkyd resin, furfuryl alcohol resin and resin emulsion and the solvent is an alcohol compound.

Preferably, in the above technical scheme, the method further comprises the following steps:

(g) the dried carbonized bamboo fence is coated with bamboo oil, an oiled carbonized bamboo fence is obtained after drying, and then the oiled carbonized bamboo fence is wiped;

The bamboo oil is prepared by conducting high-temperature pyrolysis at 400-500° C. on the bamboo material to obtain pyrolysis gas and then condensing the pyrolysis gas.

Preferably, in the above technical scheme, heating is firstly performed with flames to soften the bent parts of the raw bamboos, then an external force is exerted to forcibly straighten the raw bamboos, and finally the heated parts of the raw bamboos are cooled with water during raw bamboo straightening.

Preferably, in the above technical scheme, the mold and insect prevention liquid further contains 2-10 parts of silicate flame retardant by mass.

Preferably, in the above technical scheme, the solvent is furfuryl alcohol or polyvinyl alcohol.

Preferably, in the above technical scheme, the mold and insect prevention liquid further contains 1-10 parts of polyacrylate film-forming agent by mass.

Preferably, in the above technical scheme, borate is sodium borate or disodium octaborate.

Preferably, in the above technical scheme, the surface active agent is a mixture of an anionic surface active agent or a non-ionic surface active agent.

Preferably, in the above technical scheme, a preparation method of the mold and insect prevention liquid is as follows: the surface active agent, the solvent and the water are put in a container for stirring at normal temperature and pressure, heating is performed to reach 40-65° C., the loss-resistant agent and the antibacterial agent are added successively, and stirring is performed for 30-120 minutes to obtain the liquid.

Preferably, in the above technical scheme, the mold and insect prevention liquid further contains 2-10 parts of silicate flame retardant by mass, and the silicate flame retardant and the antibacterial agent are added simultaneously during the preparation of the mold and insect prevention liquid.

The present disclosure has the following advantages:

1, no paint is used, and no environmental pollution is caused;

2, although it is recorded in the data that poles of bamboos are straight, most of the bamboos are actually bent, limiting bamboo usage; while the raw bamboo heating and softening process is adopted and then a certain external force is applied to permanently straighten the bent parts of the raw bamboos;

3, the present disclosure adopts the special mold and insect prevention liquid, so that the mold and insect prevention effect on the bamboo fence can be kept for at least 2 years; in addition, the mold and insect prevention liquid of the present disclosure does not contain any illegal components, and there is no adverse influence on the environment and organisms;

4, after the bamboo material heat treatment of the present disclosure, secondary substances such as saccharides, quinines, flavonoids, starch and proteins in bamboos can be decomposed in a high-temperature and high-pressure environment, meanwhile fungi in the bamboos and the like can be killed, and survival fungal spores also cannot survive due to the loss of nutrition source; in addition, the bamboo material can change from a natural green color to a carbon black color and bamboos different in age and at different parts tend to be uniform in color.

DETAILED DESCRIPTION OF THE INVENTION

The specific embodiments are only for explanation of the present disclosure, not intended to limit the present disclosure and any changes, made by the person skilled in the art after the description of the present disclosure is read, within the scope claimed by Claims are protected by the patent law.

Embodiment I

A bamboo fence making method comprises the following steps:

(a) raw bamboos are straightened and cut to obtain a bamboo material having specified length, or the raw bamboos are cut to reach the specified length and then are straightened to obtain a bamboo material; heating is firstly performed with flames to soften the bent parts of the raw bamboos, then an external force is exerted to forcibly straighten the raw bamboos, and finally the heated parts of the raw bamboos are cooled with water during raw bamboo straightening.

(b) the bamboo material is put inside a hot baking room, baking is performed at the temperature of 180° C. for 3 hours, then mold and insect prevention liquid is sprayed, then cooling is performed to reach 150° C., this temperature is kept for 10 hours for heat treatment; then, the mold and insect prevention liquid is sprayed again, cooling continues to reach 50° C. and this temperature is kept for 6 hours to obtain a dried medicinal bamboo material;

(c) the dried medicinal bamboo material is punched and is serially connected by using iron wires to make a bamboo fence;

(d) the bamboo fence is put in a high-pressure carbonization furnace with the temperature of 120° C. and the air pressure of 0.2 MPa or above, heat treatment is performed for 5 hours to obtain a carbonized bamboo fence;

(e) the carbonized bamboo fence is cooled through water spraying to obtain a rehydrated carbonized bamboo fence;

(f) the rehydrated carbonized bamboo fence is dried at a low temperature of 45° C. to reach the moisture content of 18%, and a dried carbonized bamboo fence is obtained;

(g) the dried carbonized bamboo fence is coated with bamboo oil, an oiled carbonized bamboo fence is obtained after drying, and then the oiled carbonized bamboo fence is wiped.

The mold and insect prevention liquid contains, by mass, 1 part of antibacterial agent boric acid, 3 parts of loss-resistant agent alkyd resin, 1 part of film-forming agent polyacrylate, 0.1 part of anionic surface active agent, 3.5 parts of solvent furfuryl alcohol and 2 parts of water.

A preparation method of the mold and insect prevention liquid is as follows: the surface active agent, the solvent and the water are put in a container for stirring at normal temperature and pressure, heating is performed to reach 40° C., the loss-resistant agent and the antibacterial agent are added successively and stirring is performed for 120 minutes to obtain the liquid.

The bamboo oil is prepared by conducting high-temperature pyrolysis of 400-500° C. on the bamboo material to obtain pyrolysis gas and then condensing the pyrolysis gas.

Embodiment II

A bamboo fence making method comprises the following steps:

(a) raw bamboos are straightened and cut to obtain a bamboo material having specified length or the raw bamboos are cut to reach the specified length and then are straightened to obtain a bamboo material; heating is firstly performed with flames to soften the bent parts of the raw bamboos, then an external force is exerted to forcibly straighten the raw bamboos, and finally the heated parts of the raw bamboos are cooled with water during raw bamboo straightening.

(b) the bamboo material is put in a hot baking room, baking is performed at a temperature of 200° C. for 3 hours, then mold and insect prevention liquid is sprayed, then cooling is performed to reach 160° C., the temperature is kept for 9 hours for heat treatment; then, the mold and insect prevention liquid is sprayed again, cooling continues to reach 70° C. and the temperature is kept for 5 hours to obtain a dried medicinal bamboo material;

(c) the dried medicinal bamboo material is punched and is serially connected by using iron wires to make a bamboo fence;

(d) the bamboo fence is put in a high-pressure carbonization furnace with the temperature of 150° C. and the air pressure of 0.2 MPa or above, heat treatment is performed for 5 hours to obtain a carbonized bamboo fence;

(e) the carbonized bamboo fence is cooled through water spraying to obtain a rehydrated carbonized bamboo fence;

(f) the rehydrated carbonized bamboo fence is dried at a low temperature of 50° C. to reach the moisture content of 16%, and a dried carbonized bamboo fence is obtained;

(g) the dried carbonized bamboo fence is coated with bamboo oil, an oiled carbonized bamboo fence is obtained after drying, and then the oiled carbonized bamboo fence is wiped.

The mold and insect prevention liquid contains, by mass, 2 part of antibacterial agent boric acid, 1 parts of loss-resistant agent alkyd resin, 2 parts of loss-resistant agent furfuryl alcohol resin, 2 part of film-forming agent polyacrylate, 0.2 part of anionic surface active agent, 5 parts of solvent furfuryl alcohol and 2 parts of water.

A preparation method of the mold and insect prevention liquid is as follows: the surface active agent, the solvent and the water are put in a container for stirring at normal temperature and pressure, heating is performed to reach 45° C., the loss-resistant agent and the antibacterial agent are added successively, and stirring is performed for 100 minutes to obtain the liquid. The flame retardant silicate and the antibacterial agent can be added simultaneously.

The bamboo oil is prepared by conducting high-temperature pyrolysis of 400-500° C. on the bamboo material to obtain pyrolysis gas and then condensing the pyrolysis gas.

Embodiment III

A bamboo fence making method comprises the following steps:

(a) raw bamboos are straightened and cut to obtain a bamboo material having specified length or the raw bamboos are cut to reach the specified length and then are straightened to obtain a bamboo material; heating is firstly performed with flames to soften the bent parts of the raw bamboos, then an external force is exerted to forcibly straighten the raw bamboos, and finally the heated parts of the raw bamboos are cooled with water during raw bamboo straightening.

(b) the bamboo material is put inside a hot baking room, baking is performed at the temperature of 220° C. for 3 hours, then mold and insect prevention liquid is sprayed, then cooling is performed to reach 160° C., the temperature is kept for 8 hours for heat treatment; then, the mold and insect prevention liquid is sprayed again, cooling continues to reach 100° C., and the temperature is kept for 4 hours to obtain a dried medicinal bamboo material;

(c) the dried medicinal bamboo material is punched and is serially connected by using iron wires to make a bamboo fence;

(d) the bamboo fence is put in a high-pressure carbonization furnace with the temperature of 180° C. and the air pressure of 0.2 MPa or above, heat treatment is performed for 4 hours to obtain a carbonized bamboo fence;

(e) the carbonized bamboo fence is cooled through water spraying to obtain a rehydrated carbonized bamboo fence;

(f) the rehydrated carbonized bamboo fence is dried at the low temperature of 55° C. to reach the moisture content of 14%, and a dried carbonized bamboo fence is obtained;

(g) the dried carbonized bamboo fence is coated with bamboo oil, an oiled carbonized bamboo fence is obtained after drying, and then the oiled carbonized bamboo fence is wiped.

The mold and insect prevention liquid contains, by mass, 2 part of antibacterial agent boric acid, 2 parts of loss-resistant agent rosin resin, 2 parts of loss-resistant agent polyvinyl acetate, 4 parts of flame retardant silicate, 10 part of film-forming agent polyacrylate, 0.5 part of anionic surface active agent, 7 parts of solvent furfuryl alcohol and 3 parts of water.

A preparation method of the mold and insect prevention liquid is as follows: the surface active agent, the solvent and the water are put in a container for stirring at normal temperature and pressure, heating is performed to reach 50° C., the loss-resistant agent and the antibacterial agent are added successively, and stirring is performed for 90 minutes to obtain the liquid. Wherein, the flame retardant silicate and the antibacterial agent can be added simultaneously.

The bamboo oil is prepared by conducting high-temperature pyrolysis of 400-500° C. on the bamboo material to obtain pyrolysis gas and then condensing the pyrolysis gas.

Embodiment IV

A bamboo fence making method comprises the following steps:

(a) raw bamboos are straightened and cut to obtain a bamboo material having specified length or the raw bamboos are cut to reach the specified length and then are straightened to obtain a bamboo material; heating is firstly performed with flames to soften the bent parts of the raw bamboos, then an external force is exerted to forcibly straighten the raw bamboos, and finally the heated parts of the raw bamboos are cooled with water during raw bamboo straightening.

(b) the bamboo material is put inside a hot baking room, baking is performed at the temperature of 230° C. for 2 hours, then mold and insect prevention liquid is sprayed, then cooling is performed to reach 170° C., the temperature is kept for 7 hours for heat treatment; then, the mold and insect prevention liquid is sprayed again, cooling continues to reach 120° C. and the temperature is kept for 4 hours to obtain a dried medicinal bamboo material;

(c) the dried medicinal bamboo material is punched and is serially connected by using iron wires to make a bamboo fence;

(d) the bamboo fence is put in a high-pressure carbonization furnace with the temperature of 180° C. and the air pressure of 0.2 MPa or above, heat treatment is performed for 4 hours to obtain a carbonized bamboo fence;

(e) the carbonized bamboo fence is cooled through water spraying to obtain a rehydrated carbonized bamboo fence;

(f) the rehydrated carbonized bamboo fence is dried at the low temperature of 55° C. to reach the moisture content of 12% and a dried carbonized bamboo fence is obtained;

(g) the dried carbonized bamboo fence is coated with bamboo oil, an oiled carbonized bamboo fence is obtained after drying and then the oiled carbonized bamboo fence is wiped.

The mold and insect prevention liquid contains, by mass, 4 parts of antibacterial agent boric acid, 7 parts of loss-resistant agent urea resin, 6 parts of film-forming agent polyacrylate, 1 part of anionic surface active agent, 8 parts of solvent furfuryl alcohol and 4 parts of water.

A preparation method of the mold and insect prevention liquid is as follows: the surface active agent, the solvent and the water are put in a container for stirring at normal temperature and pressure, heating is performed to reach 55° C., the loss-resistant agent and the antibacterial agent are added successively and stirring is performed for 70 minutes to obtain the liquid. The flame retardant silicate and the antibacterial agent can be added simultaneously.

The bamboo oil is prepared by conducting high-temperature pyrolysis of 400-500° C. on the bamboo material to obtain pyrolysis gas and then condensing the pyrolysis gas.

Embodiment V

A bamboo fence making method comprises the following steps:

(a) raw bamboos are straightened and cut to obtain a bamboo material having specified length or the raw bamboos are cut to reach the specified length and then are straightened to obtain a bamboo material; heating is firstly performed with flames to soften the bent parts of the raw bamboos, then an external force is exerted to forcibly straighten the raw bamboos, and finally the heated parts of the raw bamboos are cooled with water during raw bamboo straightening.

(b) the bamboo material is put inside a hot baking room, baking is performed at the temperature of 240° C. for 2 hours, then mold and insect prevention liquid is sprayed, then cooling is performed to reach 180° C., the temperature is kept for 6 hours for heat treatment; then, the mold and insect prevention liquid is sprayed again, cooling continues to reach 150° C., and the temperature is kept for 3 hours to obtain a dried medicinal bamboo material;

(c) the dried medicinal bamboo material is punched and is serially connected by using iron wires to make a bamboo fence;

(d) the bamboo fence is put in a high-pressure carbonization furnace with the temperature of 200° C. and the air pressure of 0.2 MPa or above, heat treatment is performed for 3 hours to obtain a carbonized bamboo fence;

(e) the carbonized bamboo fence is cooled through water spraying to obtain a rehydrated carbonized bamboo fence;

(f) the rehydrated carbonized bamboo fence is dried at a low temperature of 60° C. to reach the moisture content of 10%, and a dried carbonized bamboo fence is obtained;

(g) the dried carbonized bamboo fence is coated with bamboo oil, an oiled carbonized bamboo fence is obtained after drying, and then the oiled carbonized bamboo fence is wiped.

The mold and insect prevention liquid contains, by mass, 5 part of antibacterial agent disodium octaborate, 4 parts of loss-resistant agent polyvinyl acetate, 4 parts of furfuryl alcohol resin, 8 parts of flame retardant silicate, 2 parts of anionic surface active agent, 9 parts of solvent furfuryl alcohol and 5 parts of water.

A preparation method of the mold and insect prevention liquid is as follows: the surface active agent, the solvent and the water are put in a container for stirring at normal temperature and pressure, heating is performed to reach 60° C., the loss-resistant agent and the antibacterial agent are added successively and stirring is performed for 50 minutes to obtain the liquid. The flame retardant silicate and the antibacterial agent can be added simultaneously.

The bamboo oil is prepared by conducting high-temperature pyrolysis of 400-500° C. on the bamboo material to obtain pyrolysis gas and then condensing the pyrolysis gas.

Embodiment VI

A bamboo fence making method comprises the following steps:

(a) raw bamboos are straightened and cut to obtain a bamboo material having specified length or the raw bamboos are cut to reach the specified length and then are straightened to obtain a bamboo material; heating is firstly performed with flames to soften the bent parts of the raw bamboos, then an external force is exerted to forcibly straighten the raw bamboos, and finally the heated parts of the raw bamboos are cooled with water during raw bamboo straightening.

(b) the bamboo material is put inside a hot baking room, baking is performed at the temperature of 250° C. for 2 hours, then mold and insect prevention liquid is sprayed, then cooling is performed to reach 180° C., the temperature is kept for 6 hours for heat treatment; then, the mold and insect prevention liquid is sprayed again, cooling continues to reach 150° C., and the temperature is kept for 3 hours to obtain a dried medicinal bamboo material;

(c) the dried medicinal bamboo material is punched and is serially connected by using iron wires to make a bamboo fence;

(d) the bamboo fence is put in a high-pressure carbonization furnace with the temperature of 200° C. and the air pressure of 0.2 MPa or above, heat treatment is performed for 3 hours to obtain a carbonized bamboo fence;

(e) the carbonized bamboo fence is cooled through water spraying to obtain a rehydrated carbonized bamboo fence;

(f) the rehydrated carbonized bamboo fence is dried at the low temperature of 60° C. to reach the moisture content of 10% and a dried carbonized bamboo fence is obtained;

(g) the dried carbonized bamboo fence is coated with bamboo oil, an oiled carbonized bamboo fence is obtained after drying and then the oiled carbonized bamboo fence is wiped.

The mold and insect prevention liquid contains, by mass, 6 parts of antibacterial agent disodium octaborate, 5 parts of loss-resistant agent rosin resin, 5 parts of phenolic resin, 10 parts of flame retardant silicate, 4 parts of anionic surface active agent, 10 parts of solvent furfuryl alcohol and 6 parts of water.

A preparation method of the mold and insect prevention liquid is as follows: the surface active agent, the solvent and the water are put in a container for stirring at normal temperature and pressure, heating is performed to reach 65° C., the loss-resistant agent and the antibacterial agent are added successively and stirring is performed for 30 minutes to obtain the liquid. The flame retardant silicate and the antibacterial agent can be added simultaneously.

The bamboo oil is prepared by conducting high-temperature pyrolysis of 400-500° C. on the bamboo material to obtain pyrolysis gas and then condensing the pyrolysis gas.

What is claimed is:

1. A bamboo fence making method, comprising the following steps:

(a) straightening a raw bamboo and then cutting it to obtain a bamboo material having a predetermined length; or cutting a raw bamboo and then straightening it to obtain a bamboo material having a predetermined length;

(b) placing the bamboo material inside a hot baking room, wherein baking is performed at a temperature of 180-250 degrees Celsius for between 2 and 3 hours and a cooked bamboo material is obtained, wherein mold and insect prevention liquid are then sprayed onto the cooked bamboo material, wherein cooling is then performed to reach 150-180 degrees Celsius, wherein the temperature is maintained for between 6 and 10 hours for heat treatment, wherein mold and insect prevention liquid is sprayed again onto the cooked bamboo material and cooling continues until the cooked bamboo material reaches 50-150 degrees Celsius, and the temperature is kept for between 3 and 6 hours to obtain a dried medicinal bamboo material;

(c) punching the dried medicinal bamboo material, wherein the dried medicinal bamboo material is serially connected by using iron wires to make a bamboo fence;

(d) placing the bamboo fence in a high-pressure carbonization furnace with a temperature of between 120 and 200 degrees Celsius and an air pressure of 0.2MPa or above, wherein heat treatment is performed for between 3 and 5 hours to obtain a carbonized bamboo fence;

(e) cooling the carbonized bamboo fence through water spraying to obtain a rehydrated carbonized bamboo fence;

(f) drying the rehydrated carbonized bamboo fence at a temperature of 45-60 degrees Celsius to reach a moisture content of between 10and 18% and a dried carbonized bamboo fence is obtained;

wherein the mold and insect prevention liquid contains, by mass, the following components:

an antibacterial agent of between 1 and 6 parts;

a loss-resistant agent of between 3 and 10 parts;

a surface active agent of between 0.1 and 4 parts;

a solvent of between 3.5 and 10 parts;

water of between 2 and 6 parts, wherein the antibacterial agent is boric acid or borate, the loss-resistant agent is one or more of phenolic resin, urea resin, polyvinyl acetate, alkyd resin, furfuryl alcohol resin and resin emulsion, and the solvent is an alcohol compound.

2. The bamboo fence making method according to claim 1, characterized by further comprising the steps wherein:

(g) coating the dried carbonized bamboo fence with bamboo oil to obtain an oiled carbonized bamboo fence after drying, and wiping the oiled carbonized bamboo fence;

wherein the bamboo oil is prepared according to the following steps:

conducting high-temperature pyrolysis of 400-500 degrees Celsius on an untreated bamboo material to obtain pyrolysis gas; condensing the pyrolysis gas, then the bamboo oil is obtained.

3. The bamboo fence making method according to claim 1, wherein heating is firstly performed with flames to soften bent parts of the raw bamboos, then an external force is exerted to forcedly straighten the raw bamboos, and the heated parts of the raw bamboos are cooled with water during raw bamboo straightening.

4. The bamboo fence making method according to claim 1, wherein the mold and insect prevention liquid further contains between 2 and 10 parts of flame retardant silicate by mass.

5. The bamboo fence making method according to claim 1, wherein the solvent is furfuryl alcohol or polyvinyl alcohol.

6. The bamboo fence making method according to claim 1, wherein the mold and insect prevention liquid further contains between 1 and 10 parts of polyacrylate film-forming agent by mass.

7. The bamboo fence making method according to claim 1, wherein the borate is sodium borate or disodium octaborate.

8. The bamboo fence making method according to claim 1, wherein the surface active agent is a mixture of an anionic surface active agent or a non-ionic surface active agent.

9. The bamboo fence making method according to claim 1, wherein the preparation method of the mold and insect prevention liquid comprises: the surface active agent, the solvent and the water are put in a container for stirring at normal temperature and pressure, heating is performed to reach between 40 and 65 degrees Celsius, the loss-resistant agent and the antibacterial agent are added successively, and stirring is performed for between 30 and 120 minutes to obtain the mold and insect prevention liquid.

10. The bamboo fence making method according to claim 9, wherein the mold and insect prevention liquid further contains between 2 and 10 parts of silicate flame retardant by mass, and the silicate flame retardant and the antibacterial agent are added simultaneously during the preparation of the mold and insect prevention liquid.

* * * * *